United States Patent [19]
Woell et al.

[11] Patent Number: 5,241,122
[45] Date of Patent: Aug. 31, 1993

[54] CATALYSTS COMPRISING GROUP IB METALS

[75] Inventors: James B. Woell, Lawrenceville, N.J.; John W. Catino, Riegelsville, Pa.

[73] Assignee: Union Camp Corporation, Wayne, N.J.

[21] Appl. No.: 845,288

[22] Filed: Mar. 3, 1992

Related U.S. Application Data

[63] Continuation-in-part of Ser. No. 744,142, Aug. 13, 1991, which is a continuation-in-part of Ser. No. 537,399, Jun. 13, 1990, abandoned.

[51] Int. Cl.$^5$ .................... C07C 45; C07C 47
[52] U.S. Cl. .................... 568/485; 568/426; 568/449; 568/470; 568/471; 568/473; 568/489
[58] Field of Search ............ 568/471, 473, 470, 485, 568/489, 426, 449

[56] References Cited

U.S. PATENT DOCUMENTS

| | | | |
|---|---|---|---|
| 3,778,477 | 12/1973 | Mueller | 568/485 |
| 4,383,124 | 5/1983 | de Graaf | 568/485 |
| 4,503,261 | 3/1985 | Sauer et al. | 568/471 |
| 4,814,513 | 3/1989 | Graft et al. | 568/471 |
| 4,816,606 | 3/1989 | Brenner et al. | 568/471 |
| 4,851,584 | 7/1989 | Graf et al. | 568/471 |

FOREIGN PATENT DOCUMENTS 1381587  1/1975  United Kingdom ............... 568/485

Primary Examiner—Werren B. Lone
Attorney, Agent, or Firm—William K. Wissing

[57] ABSTRACT

Catalysts, catalyst precursors, and catalytic systems are provided. The catalysts generally comprise a substrate that includes a group IB metal and a porous, microcrystalline layer that includes the metal and that is disposed on at least a portion of the substrate. The catalysts are prepared by providing a substrate that includes group IB metal, oxidizing said substrate in the presence of stainless steel to produce an oxide coating of said group IB metal, and reducing substantially all of said oxidized substrate.

43 Claims, 5 Drawing Sheets

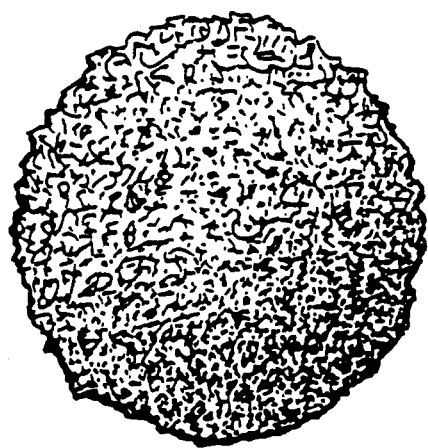
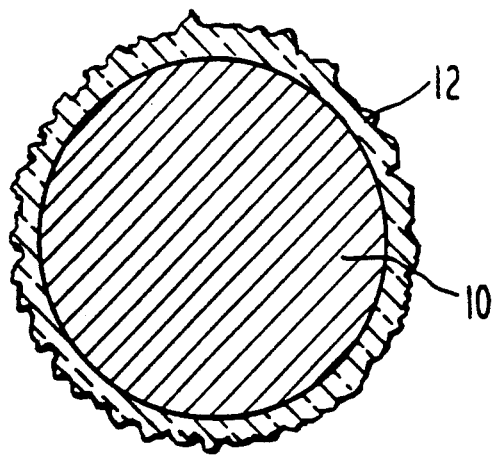
Fig. 1  Fig. 1a
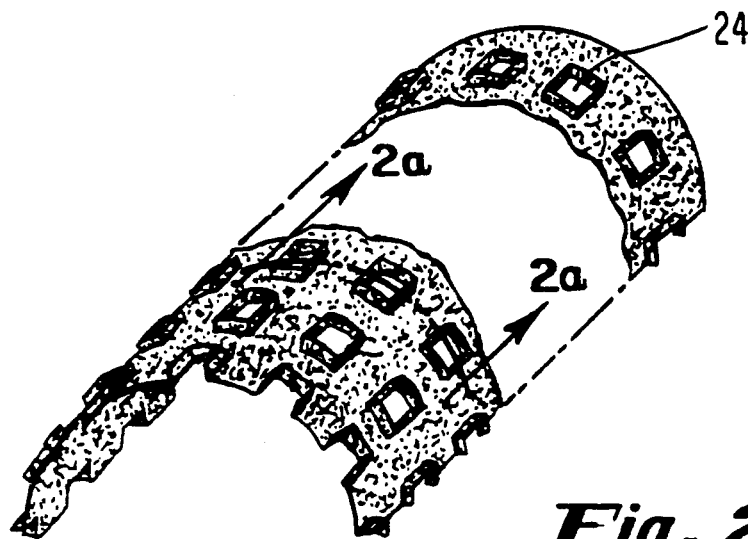
Fig. 2
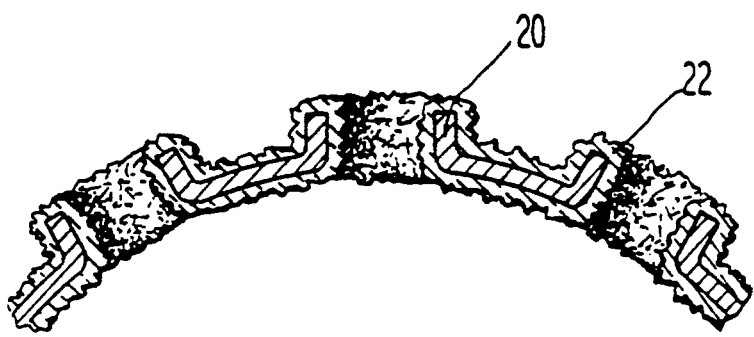
Fig. 2a

CATALYSTS COMPRISING GROUP IB METALS

CROSS-REFERENCE TO RELATED APPLICATION

This application is a continuation-in-part of U.S. application Ser. No. 744,142, filed Aug. 13, 1991, entitled "A Group IB Metal Catalyst Having a Porous, Microcrystalline Layer of a Group IB Metal Disposed Thereon", which is a continuation-in-part of application Ser. No. 537,399, filed Jun. 13, 1990 entitled "Catalyst Suitable for the Production of Aldehydes". The disclosures of both applications are incorporated herein by reference.

FIELD OF THE INVENTION

This invention relates to the field of high surface area catalysts, methods for making such catalysts, and processes for the preparation of aldehydes by vapor phase dehydrogenation of alcohols. More particularly, the invention relates to novel, high surface area, group IB catalysts and catalytic systems comprising them.

BACKGROUND OF THE INVENTION

The metals copper, silver, and gold, found in Group IB of the Periodic Table, often are employed as catalysts in the production of large quantities of valuable chemical compounds, especially aldehydes. Citral and lilestralis are two important examples of aldehydes produced using Group IB metal catalysts.

Lilestralis (p-tert-butyl-alpha-methyldihydrocinnamaldehyde, formula 1), an important fragrance ingredient, can be produced by liquid phase dehydrogenation of liliol in the presence of a group IB metal catalyst.

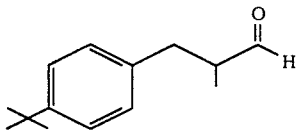

1

Generally, oxygen is not used in the conversion of liliol to lilestralis because the lilestralis product is susceptible to further oxidation to p-tert-butylbenzyl methyl ketone, which cannot be conveniently removed from the reaction mixture.

Citral (3,7-dimethyl-2,6-octadienal, formula 2) is an important ingredient in flavoring and perfumery products, especially those involving citrus formulations, and is an intermediate in the manufacture of ionones, methyl ionones, and vitamin A.

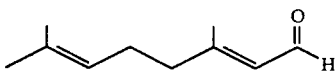

2

Citral can be produced by reacting unsaturated terpenic alcohols such as geraniol and/or nerol with an oxygen-containing gas at an elevated temperature in the presence of a copper catalyst. For example, British Patent Specification 1,381,587, which is incorporated herein by reference, discloses a method for preparing citral using as a catalyst either wire gauze formed from a group IB metal or the wire gauze plated with group IB metal. Alternatively, the metal can be carried on a non-acidic support.

High surface area copper catalysts such as Raney copper catalysts or oxidized and fresh ultrafine copper powders [Sakka, et al., "Sintering and gas desorption characteristics of copper ultrafine powders", *Materials Transactions*, vol. 31, no. 9, 802–809 (1990)] generally are believed to be unsuitable for vapor phase dehydrogenations, because their fine nature is not conducive to the free flow of gases present in such reactions. Raney catalysts can, however, be used in certain fixed bed operations. Tomsett, et al., *Applied Catalysis*, 1987, 35, 321, disclosed that a Raney catalyst having a high surface area of copper minimized problems associated with pore diffusion. These Raney catalysts are believed to be unsuitable in processes that cannot tolerate the impurities that are co-generated during production of the catalyst.

Although copper catalysts have been employed in preparing aldehydes from alcohols, the high temperatures and oxidizing conditions associated with these conversions often cause copper substrates to become brittle and degrade. For example, copper spheres can lose approximately 50% of their catalytic reactivity within one to two weeks under such conditions.

A number of catalysts based on group IB metals are known in the art. For example, U.S Pat. No. 4,480,136 discloses a process for preparing norbornyl oxyacetaldehyde using a silver or copper chromite catalyst.

U.S. Pat. No. 4,816,606 discloses a continuous process for preparing aldehydes and ketones wherein an alcohol is oxidized with oxygen in the presence of a supported catalyst composed of an inert carrier having a smooth surface and from 0.1 to 20% by weight, based on the weight of the carrier, of an active layer of copper, silver and/or gold. The active metal is applied to the inert material to provide a smooth, abrasion-resistant coating.

U.S. Pat. No. 4,503,261 discloses a process for preparing glyoxal wherein ethylene glycol, oxygen, and an inert gas are passed over a catalyst consisting of one or more layers of silver and copper crystals having a particle size of from 0.1 to 2.5 mm. The catalyst contains from 10 to 45% by weight of copper crystals and from 55 to 90% by weight of silver crystals based on the total weight of all the catalyst particles.

U.S. Pat. No. 4,560,759 discloses a process for preparing pyrroles comprising reacting ammonia or an amine with a diol in the presence of a supported catalyst containing copper, silver, zinc, palladium, nickel, cobalt and/or platinum and/or compounds of these metals. The supported catalyst comprises from 0.2 to 25% by weight active metal based on the weight of the support.

U.S. Pat. No. 4,851,584 discloses a process for preparing carbonyl compounds wherein alcohols are oxidized with an oxygen-containing gas in the presence of a catalyst containing copper and silver or alloys in which the mass fraction of copper or silver is more than 90%. The catalysts are prepared by coating an inert material with the metal by known methods such as flame coating, plasma coating or sputtering.

U.S. Pat. No. 4,814,513 discloses a process for preparing carbonyl compounds by oxidizing an alcohol with an oxygen-containing gas in the presence of a catalyst comprising copper or silver and a phosphorus compound that is volatile under the conditions of the reaction. Metallic copper or silver, copper or silver alloys, or compounds with metals or non-metals are said to be suitable as catalysts. The catalyst can be applied to an inert carrier and can be subjected to reducing treatment before use, if required.

Accordingly, a method for producing aldehydes is needed in which catalytic reactivity can be extended and the yield and purity of the final product can be improved. There is also a need for catalysts that are resistant to accelerated erosion under a variety of conditions.

SUMMARY OF THE INVENTION

The present invention provides improved group IB catalysts and catalytic systems comprising the same. The catalysts and catalytic systems exhibit surprising stability and long catalytic life in oxidative dehydrogenation reactions, particularly oxidative dehydrogenation of alcohols to form aldehydes. These properties are believed to be attributable to fine metal crystals disposed on the catalysts' surface.

The group IB catalysts have a surface area of at least about 0.04 m$^2$/g and comprise a substrate and a substantially porous, microcrystalline layer disposed on at least a portion of the substrate. In certain embodiments, the substrate and the porous, microcrystalline layer include a common group IB metal. Group IB catalysts preferably are prepared by oxidizing the substrate in the presence of stainless steel for a time sufficient to produce an oxide coating of the metal on at least a portion thereof and then reducing substantially all of the oxide coating to produce a substantially porous, microcrystalline layer. In certain embodiments such reductions are performed in the presence of stainless steel; in other embodiments they are performed in the absence of stainless steel.

The invention further provides catalyst precursors having surface area of at least about 0.04 m$^2$/g. The catalyst precursors comprise a substrate and an oxidized layer disposed upon at least a portion of the substrate. The substrate and the oxidized layer preferably are formed from a common group IB metal. The catalyst precursors preferably are prepared by oxidizing the substrate in the presence of stainless steel for a time sufficient to produce the oxide coating.

The invention also provides catalytic systems that comprise both a group IB catalyst or a catalyst precursor and stainless steel, preferably grade 316 stainless steel. The stainless steel can be present in a variety of shapes and forms, preferably as the lining of a reaction vessel or as a finely divided powder admixed with the group IB catalyst or catalyst precursor.

Further provided are processes for preparing aldehydes such as citral and lilestralis by vapor phase dehydrogenation of a corresponding alcohol in the presence of oxygen and a group IB catalyst, a catalyst precursor or a catalytic system of the invention. Where the alcohol is liliol or some other alcohol substantially free of non-aromatic, carbon/carbon double bonds, such dehydrogenations can frequently be effected with less than one equivalent of oxygen.

BRIEF DESCRIPTION OF THE DRAWINGS

The numerous objects and advantages of the present invention can be better understood by those skilled in the art by reference to the accompanying figures, in which:

FIGS. 1-1a show enlarged, elevated and cross-sectional views of a spherical substrate bearing an oxidized coating on its surface.

FIGS. 2-2a show enlarged, elevated and cross-sectional views of a porous screen substrate with an integral, oxidized coating.

DETAILED DESCRIPTION OF THE INVENTION

Figure 3:
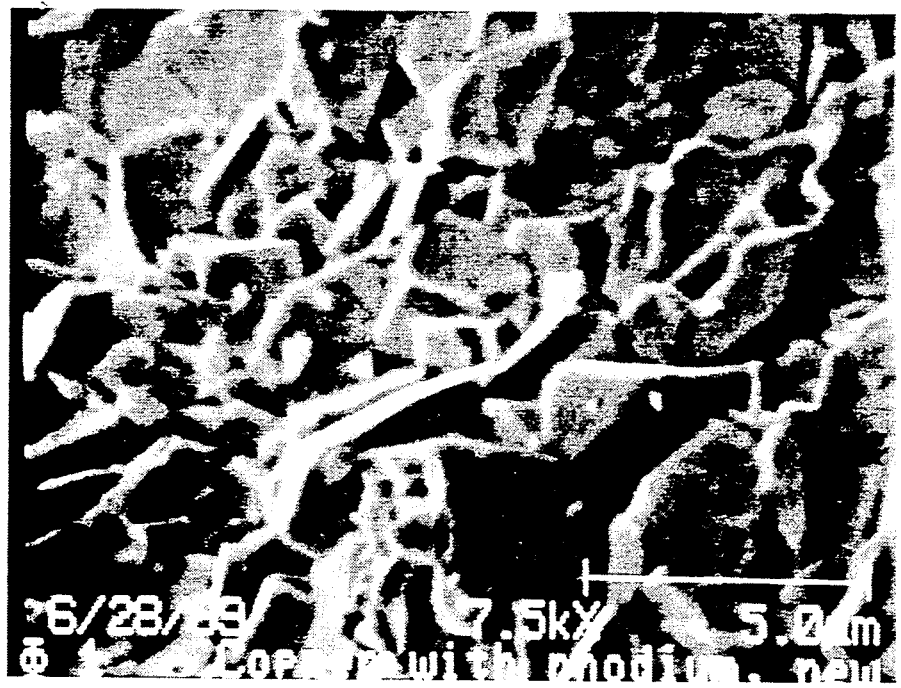
FIG. 3 is a photomicrograph at 7,500× magnification of a catalyst precursor, an oxidized copper substrate that had been treated with a RhCl$_3$ solution prior to oxidation.

The group IB catalysts of the present invention are generally in the form of a substrate that includes a group IB metal and a substantially porous, microcrystalline layer of the metal disposed on at least a portion of a substrate. The catalysts should have a surface area of at least about 0.04 m2/g, preferably at least about 0.1 m2/g. The surface area of the catalyst typically varies from about 0.04 to about 0.4 m2/g and is believed to be from about 7 to about 1000 times greater than the surface area of the substrate. The thickness of the porous, microcrystalline layer at a given point should be from about 10% to about 110% of the thickness of the substrate at that same point. The microcrystals that form the microcrystalline layer preferably have median length less than about 10 μm.

The term "substrate" as used herein refers to materials containing substantially pure group IB metals, materials containing alloys of group IB metals and other metals such as Cu/Zn and Cu/Ag alloys, and materials where group IB metals or alloys thereof are plated onto a non-acidic support such as stainless steel. Preferably, the substrate is pure copper. The shape of the substrate is not believed to be critical. Preferably, the substrate is in the shape of a sphere or a porous screen element.

In accordance with the invention, a relatively stable, substantially porous microcrystalline layer of group IB metal is disposed upon the substrate. Generally, the microcrystalline layer includes the same metal that forms or is a part of the substrate. In embodiments where the substrate is an alloy, it is believed the microcrystalline layer is primarily made up of the metal that dominates the chemistry of the alloy. It also is believed that the microcrystalline layer is metallurgically bonded to the substrate and that the substrate contains an annealed crystalline group IB metal.

The group IB catalysts of the invention appear to maintain a surface area greater than about 0.04 $m^2/g$ even after many weeks of use in dehydrogenation reactions. This extended catalyst life is surprising given the many modes of catalyst deactivation known in the art, including sintering and poisoning. While not wishing to be bound by any particular theory, it is believed that grain boundaries of the group IB metal microcrystals are pinned either by metal oxides, by other precipitates or by pores between the microcrystals, and that such pinning inhibits grain growth at the elevated temperatures to which these catalysts are exposed during use. An annealed, crystalline group IB metal substrate beneath the porous layer is believed to provide mechanical integrity to preserve the structure of the catalyst, even after extended catalytic use. Unlike many prior art group IB metal catalysts having high surface area, a catalyst bed packed with catalyst of the present invention permits the relatively free flow of gases desired in vapor phase reactions such as alcohol dehydrogenations. Due to their unique, saddle-shaped geometry, the preferred catalysts of the invention can be used as supports for other, catalytically active metals.

The group IB catalysts of the invention preferably are prepared by oxidizing a substrate containing group IB metal in the presence of stainless steel for a time sufficient to produce an oxide coating of the metal on at least a portion of the substrate. The resulting oxide-coated bodies are catalyst precursors according to the invention. Oxidation can be effected by any of the many methods known in the art. However, for rapid development of a thick, even oxidation layer it is preferred that the oxidation step include oxidizing the substrate in the presence of oxygen gas at an elevated temperature. Temperatures in the range of from about 200° C. to about 500° C. are believed to be useful.

The proportions of group IB metal substrate and of stainless steel present can vary depending on the oxidation conditions. Optimal proportions can be readily determined by those skilled in the art through routine experimentation. In general, about 1 to about 1000 $cm^2$ of stainless steel surface per 100 grams of group IB catalyst should be used, preferably about 6 to about 200 $cm^2$ of stainless steel surface per 100 grams of group IB catalyst, more preferably about 60 $cm^2$ of stainless steel surface per 100 grams of group IB catalyst.

Numerous groups and types of stainless steels are well-known in the art. It is intended that the term "stainless steel" as used herein include all known types of stainless steel. Representative stainless steels are disclosed by Mark's Standard Handbook for Mechanical Engineers, 8th edition, 1978, McGraw-Hill, New York, pp. 6-36 through 6-38. Preferred stainless steels are those belonging to Group A, the austenitic stainless steels. Preferred stainless steels comprise carbon, manganese, silicon, chromium, nickel, and molybdenum. One preferred stainless steel is AISI type No. 316, which contains up to 0.08 weight percent carbon, up to 2.0 weight percent manganese, up to 1.0 weight percent silicon, 16.0-18.0 weight percent chromium, 10.0-14.0 weight percent nickel, and 2.0-3.0 weight percent molybdenum. Molybdenum-containing stainless steels are particularly preferred. Further, it is believed that oxidation of a group IB metal substrate in the presence of a molybdenum-containing moiety, even in the absence of other components typically found in stainless steel, can provide a catalyst useful in vapor phase dehydrogenations of alcohols.

The stainless steel can be provided for the oxidation step in any of a wide variety of shapes and forms. It is presently preferred that the stainless steel be provided as the lining of a reaction vessel or as a finely divided powder admixed with the group IB catalyst or catalyst precursor. A preferred form of stainless steel (SS) powder is 316 SS PROPAK ® from Scientific Development, State College, Pa.

Preferably, the group IB metal substrate is contacted with an aqueous acid halide solution prior to oxidation. Acid halides according to the invention are halide-containing, preferably chloride-containing, moieties that yield acidic solutions when dissolved in water. Thus, acid halide solutions have pH less than 7.0, preferably less than 4.0. Such solutions should contact the substrate for a time sufficient to deposit acid halide on at least a portion of the surface of the substrate. Deposition of acid halide on the substrate can be accomplished by agitating the substrate in a dilute solution of the acid halide for several hours using a glass or stainless steel reaction vessel. Acid halide deposition can be confirmed by energy dispersive x-ray analysis. It is believed that the deposition of acid halide etches the substrate, which can be observed by visual or microscopic examination of the substrate, and facilitates rapid and even development of the oxide coating and the creation of a porous, microcrystalline layer upon reduction of the oxide coating. Suitable acid halides include HCl and acid metal chlorides such as $MnCl_2$, $ZnCl_2$, $CuCl_2$, and $RhCl_3$. Most preferred are $CuCl_2$, and $RhCl_3$.

The oxide coating must be sufficiently thick that reduction results in a substantially porous, microcrystalline metal layer having a surface area of at least about 0.04 $m^2/g$ disposed on the surface of the substrate. Table I demonstrates that the extent of the weight gain due to oxide formation and the resulting increase in surface area ($SA_{SUB}$ = surface area of copper PROPAK ® substrate, as received (0.006 $m^2/g$); $SA_{OXSUB}$ = surface area of oxidized substrate) are dependent upon the type and concentration of acid halide deposited on a substrate prior to oxidation. The substrate in Table I, 20 grams of PROPAK ® porous copper screen elements, was exposed to $O_2$ (10 ml/min) at 350° C. for 7 hours following treatment with acid halide, except as indicated.

The PROPAK ® substrate is commercially available from Scientific Development, State College, Pa.

TABLE 1

WEIGHT GAIN AND SURFACE AREA (SA) OF OXIDIZED SUBSTRATE

| Acid Halide (mMoles) | Weight Gain (grams) | $SA_{OXSUB}$ $m^2/g$ | $SA_{OXSUB}/SA_{SUB}$ |
|---|---|---|---|
| None | 0.19 | — | — |
| None[a] | 0.36 | 0.046 | 8 |
| $RhCl_3$(0.041) | 0.45 | 0.210 | 35 |
| $CuCl_2$(0.041) | 0.43 | 0.085 | 14 |
| $CuCl_2$(0.370) | 1.78 | 0.667 | 111 |
| HCl(0.117) | 0.41 | 0.153 | 25 |
| $CoCl_2$(0.211) | 1.24 | — | — |
| $ZnCl_2$(0.375) | 0.92 | — | — |
| NaCl(0.117) | 0.22 | — | — |
| $Rh(NO_3)_3$(0.116) | 0.13 | — | — |
| $CuBr_2$(0.041) | 0.14 | — | — |

[a] Oxidized for 72 hours

Catalyst precursors in the form of spheres and porous screen elements are shown in FIGS. 1-1a and 2-2a, respectively. FIGS. 1-1a show oxide coating 12 deposited on spherical substrate 10. The demarcation between oxide coating 12 and substrate 10 in FIG. 1a is shown as a line for illustrative purposes only. In practice, this demarcation can be sharp, slight or any variation therebetween, depending upon the extent of diffusion between layers, the porosity of the substrate, and/or other mechanical or metallurgical treatments employed. FIGS. 2-2a show porous screen substrate 20 bearing oxide coating 22. As will be recognized, substrate 20, which includes a plurality of apertures or windows 24, has substantially greater overall surface area than spherical elements 10. The catalyst precursors should have a surface area of at least about 0.04 m²/g, preferably at least about 0.1 m²/g. The surface area of the catalyst precursor typically varies from about 0.04 to about 1.0 m²/g, most preferably from about 0.04 to about 0.4 m²/g and is believed to be from about 7 to about 1000 times greater than the surface area of the substrate.

Reduction of the oxide layer of catalyst precursor typically is effected after the catalyst precursor has been placed in a packed bed. Preferably, the oxide layer is reduced during vapor phase dehydrogenation of an alcohol to an aldehyde. For example, reduction can be effected by oxidatively dehydrogenating geraniol and/or nerol at elevated temperatures to form citral, as generally taught by British Patent Specification 1,381,587. The group IB catalyst that results upon reduction exhibits an unexpectedly long reaction life and produces both a better yield of citral and a citral product having improved odor. Table II below provides further guidance concerning reduction of the catalyst precursor in a citral reactor. The resulting catalyst precursor (10g) was placed in a 2.5 cm diameter ×75 cm length reactor tube made from solid 316 type stainless steel. A gaseous stream of geraniol (0.75 ml/min), $O_2$ (97.4 ml/min), and steam (10 g/min water) was passed through the reactor tube at 350° C. The yield of citral is stated as an average over a testing period of two days.

TABLE II
CITRAL REACTOR STUDIES USING CATALYST PRECURSOR

| Substrate/ acid Cl | Surface Area (m2/g) oxidized/ | reduced | Change in Surface Area | Citral yield (%) |
|---|---|---|---|---|
| Cu/RhCl₃[A] | 0.137 | 0.127 | −7.3 | 52.6 |
| Cu/RhCl₃ | 0.210 | 0.043 | −79.5 | 39.4 |
| Cu/CuCl₂ | 0.085 | 0.058 | −31.8 | 42.3 |
| Cu/CuCl₂[B] | 0.667 | 0.361 | −45.9 | 53.7 |
| Cu/HCl | 0.153 | — | — | 43.8 |
| Cu | 0.046 | 0.035 | −23.9 | 45.9 |

[A]Oxidation of acid chloride-treated copper PROPAK ® performed in 316 stainless steel reactor tube. Others oxidized in a glass reactor tube as in Table I. Tested in kinetic studies for 3 months.
[B]High concentration (0.370 mmoles) of acid chloride As can be seen, surface area is lost in reducing the oxidized layer of a catalyst precursor. This loss appears to depend upon the acid halide, if any, deposited on the metal substrate before oxidation. In general, reduction decreases surface area by about 50%. Citral also was produced according to the foregoing procedure using copper PROPAK ® screens that had not been oxidized. The surface area of these screens increased upon exposure to geraniol, $O_2$, and steam (0.006 m²/g before; 0.008 m²/g after; +33% change). The yield of citral was 12.3%.

It is believed that both the reduction of the oxide layer of catalyst precursor and the vapor phase dehydrogenation of an alcohol to an aldehyde can be performed in the presence or absence of stainless steel. According to the invention, the stainless steel and the group IB catalyst precursor together, or the stainless steel and the group IB catalyst together constitute a "catalytic system", i.e. a system comprising at least one catalytic moiety.

Surprisingly, catalysts of the invention exhibit extended longevity and provide high yields of citral even after several weeks of operation. It will be recognized, however, that the present invention is not limited to the preparation of citral but, rather, includes catalysts, catalytic systems, and processes for preparing a wide variety of other aldehydes such as, for example, lilestralis, prenal, decylaldehyde, octanal, phenylacetaldehyde, benzaldehyde, and citronellal. Typically, a suitable alcohol is passed through a reaction vessel containing catalyst precursor in the presence of an oxygen-containing gas such as pure oxygen, oxygen diluted with an inert gas such as nitrogen, air, air diluted with an inert gas such as nitrogen, water vapor, pure oxygen diluted with water vapor, and combinations thereof. The oxygen-containing gas can be heated and combined with a separately heated, pre-evaporated stream of pure alcohol or an alcohol-containing mixture. Alcohol also can be inserted into a hot air stream in liquid form and permitted to vaporize. It is further understood that steam can be used in the processes of the invention, preferably at pressures greater than about 200 mm Hg.

As will be recognized by those skilled in the art, the present invention can be adapted and modified by varying reaction conditions such as temperatures, pressures, contact times, oxygen to alcohol ratios, flow rates, and catalyst bed lengths. For example, reactor pressures for preparing citral can be from about 1 to about 10,000 mm of mercury, preferably from about 4 to about 760 mm of mercury. The mole fraction, the percentage of organic raw material in a mixture of reactants, can be from about 1 to about 90%, preferably from about 5 to about 70%. Reactor temperature can be from about 275° C. to about 600° C., preferably from about 300° C. to about 500° C. Although adiabatic reactions are typical for producing citral, this invention also includes isothermal reaction processes. The contact or residence time (i.e., the amount of time raw materials are exposed to one another under the reaction conditions) will also vary depending on operating conditions such as pressure and temperature. Contact times in the range of from about 0.1 to about 30 seconds give satisfactory results, contact times of from about 0.4 to about 20 seconds give improved results Contact times of from about 0.5 to about 1.0 second are preferred; contact times of about 0.7 second are particularly preferred.

When a copper precursor catalyst (i.e., copper substrate bearing an oxide layer) is contacted with geraniol, a catalyst "break-in" period ensues during which the conversion of geraniol to citral substantially reduces the oxide layer in situ. It is believed that such in situ reduction reduces the surfaces area of the catalyst but reveals more highly active copper surfaces After "break-in" periods of about 1 to 2 days, catalysts of the invention appear to maintain these highly active surfaces for extended periods of time, i.e., at least about 6 weeks.

Preferred group IB catalysts of the invention include a copper substrate and a substantially porous microcrystalline copper surface layer disposed upon the substrate. The microcrystalline layer includes a plurality of protruding microcrystals having median length less than about 10 μm, preferably less than about 5 μm. As used herein, the term "median length" refers to a numerical median of the longest length of each of the crystals.

Surprisingly, it has been discovered that certain oxidative dehydrogenation reactions can be run with non-stoichiometric amounts of oxygen using the catalysts and catalytic systems of the invention. It appears that oxidative dehydrogenation of an alcohol to an aldehyde can be effected with less than one equivalent of oxygen where the alcohol is substantially free of non-aromatic, carbon/carbon double bonds. According to this invention an alcohol is substantially free of non-aromatic, carbon/carbon double bonds when it contains no carbon/carbon double bond that is hydrogenated during oxidative dehydrogenation of the alcohol to an aldehyde. Preferably, the alcohol contains no non-aromatic, carbon/carbon double bond within 4 carbons of its defining C—OH functionality (i.e., closer than its delta (δ) position). More preferably, the alcohol contains no non-aromatic, carbon/carbon double bond within 2 carbons of its defining C—OH functionality (i.e., closer than its beta (β) position). For example, it has been found that one equivalent of liliol can be converted to lilestralis in 52% yield in the presence of a catalyst or catalytic system using as little as 0.1 equivalent of oxygen.

Additional objects, advantages, and novel features of this invention will become apparent to those skilled in the art upon examination of the following examples, which are not intended to be limiting.

EXAMPLE I

Preparation Of A Group IB Catalyst Based On Copper Spheres

Copper spheres (400 g) were placed in a 100 ml flask. A solution comprising 300 mg of the acid chloride $RhCl_3$ in 2 ml of distilled water was added to the flask via a microinjection pump at a rate of about 16.7 μl/min. The mixture was mechanically stirred for about 6 hours to insure deposition of acid chloride on the copper spheres. The mechanical stirrer was removed and the stoppers on the flask were removed to allow the copper spheres to dry sufficiently.

When dry, the copper spheres filled about 57 cm. of a 79 cm. long (1.3 cm. diameter) reactor tube made from solid 316 type stainless steel. The copper spheres were oxidized in a stream of pure $O_2$ (100 ml/min) at 370° C. for about 66 hours. The resulting catalyst precursor is shown in FIGS. 1, 1a and 3.

EXAMPLE II

Preparation Of A Group IB Catalyst Based On Copper Screen Elements

Copper PROPAK ® (150 g; surface area = about 0.006 m²/g) was placed in a 1,000 ml 1-neck round bottom flask and a solution of 67 mg of $RhCl_3$ in about 300 ml of distilled water was added thereto. The mixture was placed on a rotary evaporator for about one hour. The rotary evaporator was set at 126 rpms for the first 40 minutes and at 31 rpms for the final 20 minutes. During this time, there was no vacuum applied. Starting from 25 mmHg at 25° C., a slight vacuum was applied over a period of about 3.5 hours to substantially dry the contents. The aqueous phase of the mixture turned an olive green and was very turbid. The copper PROPAK ® appeared green until the end of the dehydration and then became brown as it dried.

When dry, a 130 g portion of the copper screen elements was packed in a 2.5 cm. diameter ×75 cm length reactor tube made from solid 316 type stainless steel and oxidized in a stream of pure $O_2$ (100 ml/min) at 350° C. for about 18 hours. The resulting catalyst precursor is shown in FIGS. 2 and 2a.

EXAMPLE III

Comparative Preparation of Citral

A 400 g portion of the catalyst precursor prepared in Example I was placed in about 57 cm. of a 79 cm. long (1.3 cm. diameter) reactor tube made from solid 316 type stainless steel. The catalyst precursor was reduced by passing a gaseous stream of geraniol and nerol (65% geraniol/35% nerol; 489 mg/min, 3.17 mmol/min), $O_2$ (63 ml/min, 2.8 mmol/min), and steam (6.1 ml/min water) through the reactor tube at 375° C. (external sand bath temperature) to produce citral. This reaction was also performed using the catalyst precursor prepared as in Example II and the copper spheres prepared by analogy with the process described by British Patent Specification 1,381,587, respectively, in place of the catalyst precursor of Example I.

The catalyst of Example I lasted approximately 6 weeks with no significant drop in the yield of citral. The prior art copper spheres lost approximately 50 % of their catalytic reactivity within about 1 to 2 weeks. The improved longevity of the catalyst of Example I makes it ideal for an isothermal reaction in which catalyst change-out (i.e., removal and replacement) is a time consuming and costly task.

Figure 4:
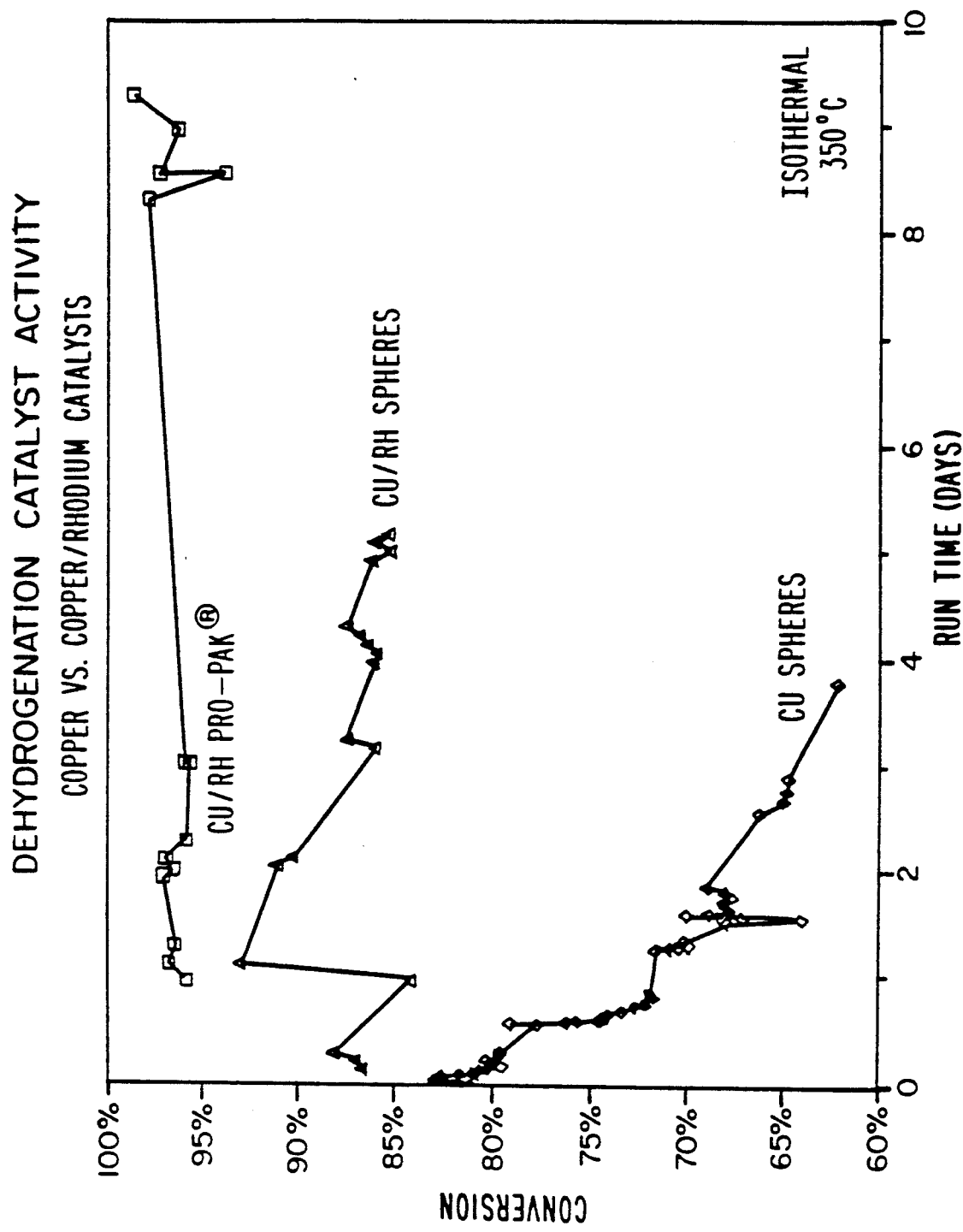
FIG. 4 shows a graph of dehydrogenation catalyst activity expressed in percent conversion versus run time for: prior art copper sphere catalysts (diamonds); copper sphere catalysts of the invention having a porous microcrystalline layer of copper disposed on the surface of the spheres (triangles); and another catalyst of the invention, a porous copper screen substrate having a porous microcrystalline layer of copper disposed on the surface of the screen (squares).
Figure 5:
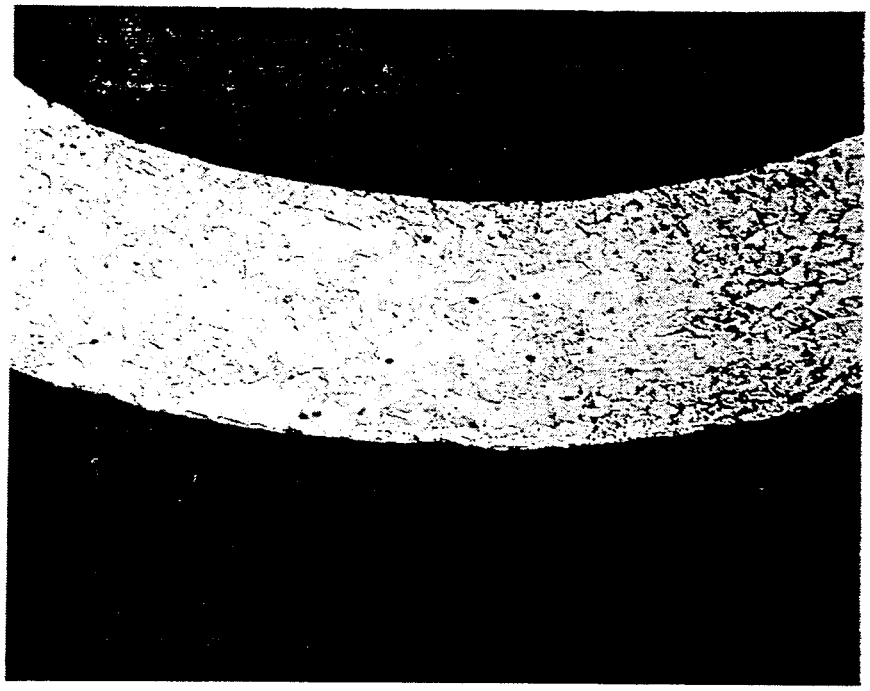
FIG. 5 is a cross-sectional photomicrograph at 400× magnification of an etched prior art copper screen catalyst.

As shown in FIG. 4, the catalyst of Example II (squares) performed extremely well with a lower pressure drop and improved yield than the similarly treated copper spheres of Example I (triangles). This is believed to be due, in part, to the fact that the latter has 5.7 times more surface area and much greater void volume.

When oxidized copper PROPAK ® having about a 10 to 30 μm thick copper oxide outer layer is first introduced in the geraniol to citral process, the reaction initially is a bit less selective than optimum. This is believed to be due to a catalyst break-in period in which the copper oxide layer is substantially reduced in situ, decreasing its surface area but revealing more highly active copper surfaces to the reaction. After the "break-in" period, usually 1 to 2 days, the copper catalyst maintains this highly active surface for extended periods of time, i.e., at least about 3 months.

With reference to FIG. 4, there is shown a comparison of the dehydrogenation catalyst activity for spherical copper particles versus the novel multi-layer catalysts of this invention. As can be seen, the untreated copper spheres (diamonds) initially produced a yield of between 80 and 85 mole percent (i.e., moles of geraniol consumed per mole of geraniol introduced) but steadily decreased within a period of about 3 days. This is believed to be due to oxidation and corrosion of the surface of the copper catalyst. However, when copper sphere catalysts of the invention (Example II, triangles) were used, an increased yield of greater than about 85 mole percent was registered. Unexpectedly, this yield continued more than 40 days into the run time (data not illustrated). The catalyst of Example II (squares) achieved a conversion yield of about 95 mole percent or better and performed at this level over 30 days of the run time before the experiment was terminated.

EXAMPLE IV

Preparation and Use of Catalyst Precursor To Produce Citral $CuCl_2.2H_2O$ (0.1437 g) was mixed with 520 ml water until dissolved. Copper PROPAK ® (260.04 g) was added to the solution in a 2 liter, one-neck round bottom flask and put onto a rotary evaporator. The flask was left stirring at room temperature with no vacuum for 2 hours. Then vacuum was set at 20 mmHg for 2 hours and full vacuum for 2 hours. The flask was then removed and stored at room temperature. A 114.61 g portion of the resulting screen elements was packed in a 2.5 cm. diameter ×75 cm. length reactor tube made from solid 316 type stainless steel. The screen elements were oxidized with an $O_2$ stream (100 ml/min) at 350° C. for 7 hours.

The resulting catalyst precursor was reduced by passing a gaseous stream of geraniol and nerol (65% geraniol/35% nerol; 670 mg/min, 4.3 mmol/min), $O_2$ (73 ml/min, 3.3 mmol/min), and steam (10 ml/min water) through the reactor tube at 360° C. to produce citral in 80% yield (moles of citral produced per mole of nerol/geraniol introduced; determined by capillary weight percent gas chromatograph).

EXAMPLE V

Preparation of Lilestralis

A 5.0 gram portion of the screen element catalyst used to produce citral in Example IV was packed in a 0.9 cm. (diameter) ×12.5 cm. (length) glass reactor tube. A gaseous stream of liliol (43.5 µl/min, 0.218 mmol/min), $O_2$ (0.22 ml/min, 0.0098 mmol/min), nitrogen (5.0 mlmin), and steam (0.5 ml/min water) was passed through the reactor at 400° C. This procedure produced lilestralis in 52% yield, with the remaining 48% of liliol recovered unchanged according to standard weight percent gas chromatography. As will be recognized, lilestralis can be separated from liliol by distillation and the unreacted liliol recycled. The level of undesirable tert-butylbenzyl methyl ketone was either zero or approached the limits of detection using gas chromatography.

Figure 6:
FIG. 6 is a cross-sectional photomicrograph at 400× magnification of an etched catalyst of the invention having a porous microcrystalline layer disposed on the surface of a copper screen substrate magnified at 400× and etched.
Figure 7:
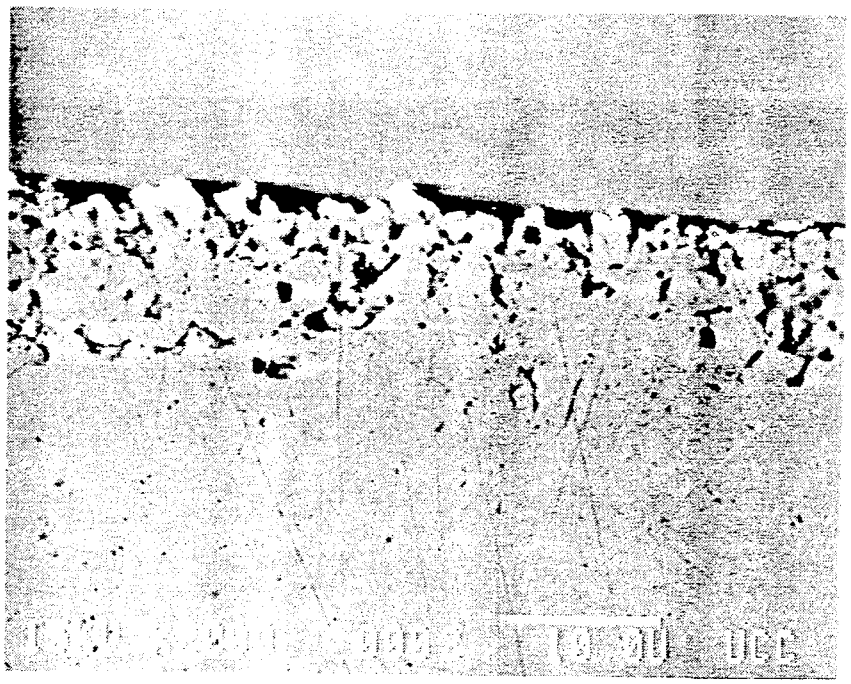
FIG. 7 is a cross-sectional photomicrograph at 2000× magnification of an etched catalyst of the invention having a porous microcrystalline layer disposed on the surface of a copper screen substrate.
Figure 8:
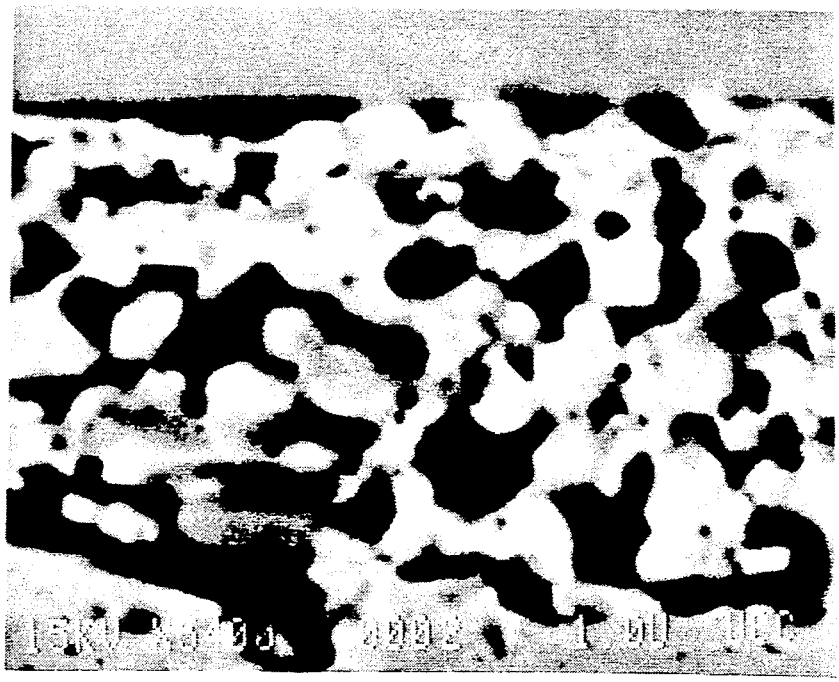
FIG. 8 is a cross-sectional photomicrograph at 5400× magnification of a catalyst of the invention showing a porous microcrystalline layer.

Referring now to the photomicrographs of FIGS. 5-8, FIG. 5 shows a cross section of a copper PROPAK ® catalyst and illustrates the regular, relatively smooth surface of the catalyst (approx. 80 µM diameter). FIG. 6 illustrates a cross section of a catalyst of the invention made according to the procedure of Example II and subsequently reduced in the citral process. It clearly shows the substantially porous, microcrystalline layer disposed on a group IB metal substrate (copper PROPAK ®). A further magnified view of the porous microcrystalline layer is shown in FIG. 7. The surface crystalline structures are believed to be responsible for the substantial increase in surface area of the catalyst of the invention. FIG. 8 provides an even further magnification of a cross section of the porous microcrystalline layer.

The catalysts shown in FIGS. 6-8 were exposed to geraniol at the entrance end of the fluidized bed and underwent a substantial reduction during the introduction period. This reduction process converted oxidized copper to copper metal while preserving a significant portion of the increased surface area. This surface area, typically greater than about 0.04 $m^2/g$, is believed to be responsible for the increased longevity of the catalysts, catalyst precursors, and catalytic systems of this invention.

What is claimed is:

1. A process for preparing an aldehyde, comprising contacting an alcohol in a vapor phase with a group IB catalyst for a time and under reaction conditions effective to dehydrogenate said alcohol, wherein:
   said alcohol is substantially free of non-aromatic, carbon/carbon double bonds; and
   said group IB catalyst has a surface area of at least about 0.04 $m^2/g$ and comprises:
   a substrate that includes a metal selected from copper, silver or gold; and
   a substantially porous, microcrystalline layer that includes said metal and that is disposed on at least a portion of said substrate.

2. The process of claim 1 wherein said catalyst has a surface area from about 0.04 to about 0.4 $m^2/g$.

3. The process of claim 1 wherein said alcohol and said catalyst are contacted in the presence of steam.

4. The process of claim 1 wherein said contacting is effected in the presence of stainless steel.

5. The process of claim 1 wherein said contacting is effected in the presence of type 316 stainless steel.

6. The process of claim 1 wherein said metal is copper.

7. The process of claim 1 wherein said aldehyde is lilestralis and said alcohol comprises liliol.

8. The process of claim 1 wherein said alcohol contains no non-aromatic, carbon/carbon double bonds closer than its beta position.

9. The process of claim 1 wherein said alcohol and said catalyst are contacted in the presence of oxygen.

10. The process of claim 8 wherein said alcohol and said catalyst are contacted in the presence of oxygen.

11. The process of claim 9 wherein one equivalent of said alcohol is contacted with said catalyst in the presence of less than one equivalent of said oxygen.

12. The process of claim 10 wherein one equivalent of said alcohol is contacted with said catalyst in the presence of less than one equivalent of said oxygen.

13. The product of the process of claim 1.

14. A process for preparing lilestralis, comprising mixing liliol and oxygen in a vapor phase in the presence of a group IB catalyst having a surface area of at least about 0.04 $m^2/g$, said catalyst comprising:
   a substrate that includes a metal selected from copper, silver or gold; and
   a substantially porous, microcrystalline layer that includes said metal and that is disposed on at least a portion of said substrate.

15. The process of claim 14 wherein said catalyst has a surface area of from about 0.04 to about 0.4 $m^2/g$.

16. The process of claim 14 wherein one equivalent of said liliol is mixed with at least one equivalent of said oxygen.

17. The process of claim 14 wherein one equivalent of said liliol is mixed with less than one equivalent of said oxygen.

18. The process of claim 14 wherein said mixing is effected in the presence of stainless steel.

19. The product of the process of claim 14.

20. A process for preparing an aldehyde, comprising contacting an alcohol in a vapor phase with a group IB catalyst precursor for a time and under reaction conditions effective to dehydrogenate said alcohol, wherein:
   said alcohol is substantially free of non-aromatic, carbon/carbon double bonds; and said group IB catalyst precursor has a surface area of at least about 0.04 $m^2/g$ and comprises:

a substrate that includes a metal selected from copper, silver or gold; and an oxidized layer that includes said metal and that is disposed on at least a portion of said substrate.

21. The process of claim 20 wherein said catalyst precursor has a surface area of from about 0.04 to about 1.0 $m^2/g$.

22. The process of claim 20 wherein said alcohol and said catalyst precursor are contacted in the presence of steam.

23. The process of claim 20 wherein said contacting is effected in the presence of stainless steel.

24. The process of claim 20 wherein said contacting is effected in the presence of type 316 stainless steel.

25. The process of claim 20 wherein said metal is copper.

26. The process of claim 20 wherein said aldehyde is lilestralis and said alcohol comprises liliol.

27. The process of claim 20 wherein said alcohol contains no non-aromatic, carbon/carbon double bond closer than its beta position.

28. The process of claim 20 wherein said alcohol and said catalyst precursor are contacted in the presence of oxygen.

29. The process of claim 27 wherein said alcohol and said catalyst precursor are contacted in the presence of oxygen.

30. The process of claim 28 wherein one equivalent of said alcohol is contacted with said catalyst precursor in the presence of less than one equivalent of said oxygen.

31. The process of claim 29 wherein one equivalent of said alcohol is contacted with said catalyst precursor in the presence of less than one equivalent of said oxygen.

32. The product of the process of claim 20.

33. A process for preparing an aldehyde comprising dehydrogenating an alcohol in a vapor phase in the presence of a catalyst having a surface area of at least about 0.04 $m^2/g$, said catalyst comprising:

a substrate that includes a metal selected from copper, silver or gold; and a substantially porous, microcrystalline layer that includes said metal and that is disposed on at least a portion of said substrate.

34. The process of claim 33 wherein said catalyst has a surface area of from about 0.04 to about 0.4 $m^2/g$.

35. The process of claim 33 wherein said catalyst has a surface area of at least about 0.1 $m^2/g$.

36. The process of claim 33 wherein said catalyst has a surface area of from about 7 to about 1000 times the surface area of the substrate.

37. The process of claim 33 wherein said porous, microcrystalline layer has a thickness of from about 10 to about 110 percent of the thickness of the substrate.

38. The process of claim 33 wherein said porous, microcrystalline layer is disposed on substantially the entire surface of said substrate.

39. The process of claim 33 wherein said metal is copper.

40. The process of claim 33 wherein said substrate is in the form of a porous screen element.

41. The process of claim 33 wherein said microcrystalline layer comprises microcrystals of median length less than about 10 $\mu m$.

42. The process of claim 33 wherein said aldehyde is citral and said alcohol comprises geraniol, nerol or mixtures thereof.

43. The process of claim 33 wherein said vapor phase dehydrogenation comprises an oxidative reaction with heat exchange or steam quench cooling.

* * * * *